United States Patent
Warken et al.

(10) Patent No.: US 8,879,148 B2
(45) Date of Patent: Nov. 4, 2014

(54) PULSE COMBINER FOR THE VARIOUS SPECTRAL COLORS OF A SUPERCONTINUUM LASER PULSE

(75) Inventors: Arno Florian Warken, Abtsteinach (DE); Hilmar Gugel, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 187 days.

(21) Appl. No.: 13/402,007

(22) Filed: Feb. 22, 2012

(65) Prior Publication Data

US 2012/0218631 A1    Aug. 30, 2012

(30) Foreign Application Priority Data

Feb. 24, 2011    (DE) .................... 10 2011 000 905

(51) Int. Cl.
| | |
|---|---|
| *G02B 21/06* | (2006.01) |
| *G02B 21/00* | (2006.01) |
| *G01J 3/02* | (2006.01) |
| *G01J 3/10* | (2006.01) |
| *G01J 3/44* | (2006.01) |
| *G01N 21/64* | (2006.01) |

(52) U.S. Cl.
CPC ........... *G02B 21/0032* (2013.01); *G01J 3/0205* (2013.01); *G01J 3/10* (2013.01); *G01J 3/0218* (2013.01); *G01N 21/6408* (2013.01); *G02B 2207/114* (2013.01); *G01J 3/4406* (2013.01); *G02B 21/0076* (2013.01); *G01N 21/6458* (2013.01)
USPC .......................................... 359/385; 359/388

(58) Field of Classification Search
USPC ................................. 359/385–390
See application file for complete search history.

(56) References Cited

U.S. PATENT DOCUMENTS

| | | | | |
|---|---|---|---|---|
| 6,020,988 | A * | 2/2000 | Deliwala et al. | 359/276 |
| 6,864,975 | B2 * | 3/2005 | Itoh et al. | 356/317 |
| 6,867,919 | B2 * | 3/2005 | Seyfried | 359/618 |
| 7,821,633 | B2 * | 10/2010 | Jalali et al. | 356/301 |
| 7,995,271 | B2 | 8/2011 | Kubo | |
| 8,237,122 | B2 * | 8/2012 | Fermann et al. | 250/341.1 |
| 8,432,543 | B2 * | 4/2013 | Frankel | 356/301 |

(Continued)

FOREIGN PATENT DOCUMENTS

| | | |
|---|---|---|
| DE | 19755361 A1 | 6/1988 |
| DE | 10115486 A1 | 12/2001 |

(Continued)

OTHER PUBLICATIONS

Pricking, S., et al., "Tailoring the soliton and supercontinuum dynamics by engineering the profile of tapered fibers," Optics Express, Sep. 13, 2010, pp. 20151-20163, vol. 18, No. 19.

(Continued)

*Primary Examiner* — Frank Font
(74) *Attorney, Agent, or Firm* — Patentbar International, P.C.

(57) ABSTRACT

An illumination device (20) for a microscope (40) has a laser unit (24) that generates at least one broadband laser light pulse (30); light components (71, 72, 73, 74, 75, 76) of different wavelengths of said broadband laser light pulse (30) being offset in time from one another. A compensation unit (36) disposed in the path of the broadband laser light pulse (30) temporally offsets the light components (71, 72, 73, 74, 75, 76) of the broadband laser light pulse (30) in such a way that they exit the compensation unit (36) simultaneously or nearly simultaneously.

10 Claims, 3 Drawing Sheets

(56) References Cited

U.S. PATENT DOCUMENTS

| | | | |
|---|---|---|---|
| 2004/0190134 A1* | 9/2004 | Tahara et al. | 359/386 |
| 2006/0237666 A1 | 10/2006 | Kubo | |
| 2008/0260319 A1 | 10/2008 | Taira et al. | |
| 2010/0188496 A1* | 7/2010 | Xie et al. | 348/79 |
| 2013/0148128 A1* | 6/2013 | Fermann et al. | 356/450 |

FOREIGN PATENT DOCUMENTS

| | | |
|---|---|---|
| DE | 10115509 A1 | 12/2001 |
| DE | 10259443 A1 | 7/2004 |
| EP | 1986030 A1 | 10/2008 |
| EP | 2423727 A1 | 2/2012 |
| EP | 2458750 A2 | 5/2012 |

OTHER PUBLICATIONS

Travers, J. C., et al., "Optical pulse compression in dispersion decreasing photonic crystal fiber," Optics Express, Oct. 1, 2007, pp. 13203-13211, vol. 15, No. 20.

Fu, L., et al., "Fibre-optic nonlinear optical microscopy and endoscopy," Journal of Microscopy, Jun. 3, 2007, pp. 195-206, vol. 226, The Royal Microscopical Society.

Lako, S., et al., "Pulse compression of nanojoule pulses in the visible using microscructure optical fiber and dispersion compensation," Applied Physics B: Lasers and Optics, 2003, pp. 267-275, vol. 76.

* cited by examiner

PULSE COMBINER FOR THE VARIOUS SPECTRAL COLORS OF A SUPERCONTINUUM LASER PULSE

RELATED APPLICATIONS

This application claims priority to German Patent Application No. DE 10 2011 000 905.1, filed Feb. 24, 2011, which is incorporated herein by reference in its entirety.

FIELD OF THE INVENTION

The present invention relates to an illumination device for a microscope and a microscope. Moreover, the present invention relates to a method for producing an illuminating light beam for a microscope.

BACKGROUND OF THE INVENTION

Microscopic methods for examining objects, in particular samples or tissue samples, sometimes require illumination devices, in particular, laser devices, which are capable of producing laser light of different wavelengths. Some microscopy methods require the illumination device to provide laser light of different wavelengths simultaneously. Supercontinuum lasers, also referred to as white-light lasers or broadband laser light sources, are suitable for this purpose. These lasers produce laser light over a broad spectrum, in particular continuously over a plurality of colors, especially ones that are visible and distinguishable by the eye, so that the broadband laser light produced appears to the eye as white light.

The white laser light can be produced in various ways. For example, the light of a conventional laser which produces laser light in a very small wavelength range, especially laser light of a single wavelength, may be coupled into an optical element which broadens the spectrum of the laser beam in the desired way. Suitable for this purpose is an optical element which is specifically designed to broaden the spectrum of the laser light beam as opposed to conventional optical elements, such as lenses, where the broadening of the spectrum is an undesired side effect. In particular, it is known to design light-conducting fibers in such a way that when light is passed therethrough, strong non-linear optical effects are produced which broaden the monochromatic laser light spectrally, converting it into white laser light. During the spectral broadening, it is normal for dispersion effects to occur, affecting the white laser light produced.

German Patent Application DE 101 15 486 A1 describes an entangled-photon microscope having a light source and an objective. The entangled-photon microscope has a microstructured optical element disposed between the light source and the objective and capable of producing entangled photons therein, the entangled photons propagating in a beam inside and outside the microstructured optical element. The microstructured optical element is constructed from a plurality of micro-optical structure elements which have at least two different optical densities. The micro-optical structure elements are, for example, cannulas, webs, honeycombs, tubes or cavities. Alternatively, or in addition, the microstructured optical element may have alternating regions of homogeneous and inhomogeneous structure. Alternatively or additionally, the microstructured optical element is formed of adjacent glass or plastic materials and cavities, and is configured as a light-conducting fiber. The fibers can be produced by extending glass tubes or glass blocks arranged in a pattern.

German Patent Application DE 101 15 509 A1 describes a confocal microscope which uses an optical device for spectral broadening of a laser pulse generated by a pulsed laser. The pulsed laser generates a pulsed laser beam which is passed through the optical device. The optical device includes a photonic-band-gap material which converts the narrow-band pulsed laser beam into illuminating light of broad spectral bandwidth.

SUMMARY OF THE INVENTION

It is an object of the present invention to provide an illumination device for a microscope, a microscope, and method for producing an illuminating light beam for a microscope, which will provide an illuminating light beam illuminating light beam suitable for illuminating samples for accurate microscopic methods.

This object is achieved by the features of the independent claims. Advantageous embodiments are described in the dependent claims.

In a first aspect, the present invention features a laser unit that generates at least one broadband laser light pulse; light components of different wavelengths of said broadband laser light pulse being offset in time from each other. A compensation unit is disposed in the path of the broadband laser light pulse to temporally offset its light components in such a way that they exit the compensation unit simultaneously or nearly simultaneously.

As a result of the time offset compensation performed by the compensation unit, the temporal distribution of the white-light laser pulse emerging from the illumination device is particularly narrow. This helps that the broadband laser light pulse, once it has exited the illumination device, can be used for highly time-resolved microscopic measurement, for example, for Fluorescence Lifetime Imaging (FLIM), particularly FLIM using multiple wavelengths.

In this context, the statement that the laser light pulse is broadband means that it has wavelengths which are continuously distributed over a larger wavelength interval, for example, over a plurality of color intervals that are visible and/or distinguishable by the naked eye. The broadband laser light pulse is also referred to as supercontinuum laser light pulse or white-light laser pulse. In this context, the statement that the light components of the broadband laser light pulse exit the compensation unit simultaneously or nearly simultaneously means that the time offset at which the light components exit the compensation unit is less than the lower time-resolution limit of the detector of the microscope. This means that there may, in fact, be a time offset after passage through the compensation unit, but the time offset is so small that the light pulses arriving at the detector are detected as arriving simultaneously. The time offset occurring in the compensation unit is achieved using dispersion effects in the compensation unit. The dispersion effects occurring in the compensation unit are opposite to those arising during the generation of the broadband laser light pulse. For example, normal dispersion may occur during the generation of the broadband laser light pulse, while anomalous dispersion may occur during compensation.

The laser unit may be part of a laser device which includes further laser units in addition to this one. Similarly, the compensation unit may form part of a compensation device which includes a plurality of compensation units.

In an advantageous embodiment, there is provided an optical element which separates narrow spectral wavelength bands of laser light from the broadband laser light pulse, so that, after passage through the optical element, the light components are offset in time from one another, spectrally limited, and spectrally spaced apart from one another. In other words, light components of different wavelength intervals are separated by the optical element from the white-light laser pulse, and thus are each spectrally limited. Thus, gaps are formed between the individual, spectrally limited light components in the previously continuous wavelength spectrum, so that these light components are spectrally spaced apart from one another. Due to the time offset between the light components of different wavelengths of the white-light laser pulse, the spectrally limited and spaced-apart light components are also offset in time from one another.

In another advantageous embodiment, the compensation unit includes a compensation element in the form of a microstructured light-conducting fiber. The microstructured light-conducting fiber may also be referred to as photonic crystal fiber or mictrostructured optical fiber of high nonlinearity. The microstructured light-conducting fiber may have cannulas, webs, honeycombs, tubes or other cavities or light-conducting spaces. In particular, the microstructured light-conducting fiber may have a glass core or an air core.

In another advantageous embodiment, the compensation unit includes an ultra-thin glass fiber or a tapered fiber as a compensation element.

In an advantageous embodiment, the dispersion of the microstructured light-conducting fiber is mainly determined by the structure and/or length thereof. For example, the diameter of the microstructured light-conducting fiber may taper to a predetermined diameter at a predetermined length. In this connection, it may be advantageous for the structure of the microstructured light-conducting fiber to change adiabatically. The adiabatic nature of such a change allows for lossless wave conduction. Furthermore, it may be convenient for the microstructured light-conducting fiber not to be rotationally symmetrical in design so as to maintain the polarization of laser light pulse.

In a second aspect, the present invention features a microscope for examining an object. The microscope is coupled to the illumination device and may be configured as a confocal scanning microscope.

In a third aspect, the present invention features a method for producing an illuminating light beam for a microscope, in which method a broadband laser light pulse is generated. The broadband laser light pulse has light components of different wavelengths which are offset in time from one another. The broadband laser light pulse, and specifically the light components thereof, are coupled into a compensation unit. The compensation unit temporally offsets the light components in such a way that they exit the compensation unit simultaneously or nearly simultaneously.

BRIEF DESCRIPTION OF THE DRAWINGS

Exemplary embodiments of the present invention are described in more detail below with reference to schematic drawings, in which.

DETAILED DESCRIPTION OF THE PREFERRED EMBODIMENTS

Figure 1:
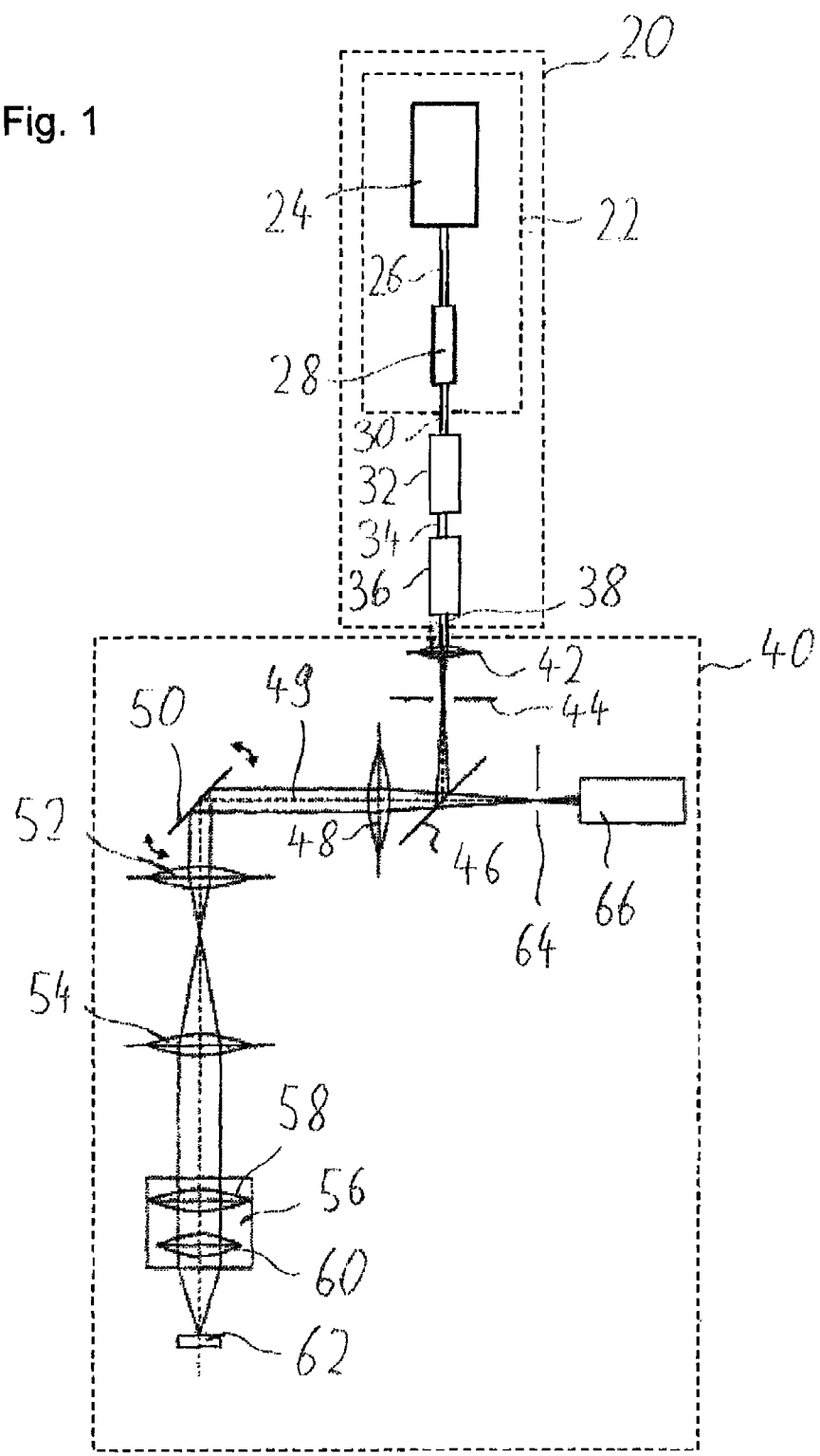
FIG. 1 is a view showing an illumination device and a microscope.

FIG. 1 shows an illumination device 20 and a microscope 40. Illumination device 20 has a laser device 22 including a laser unit 24. Alternatively, laser device 22 may have a plurality of laser units 24. Laser unit 24 generates monochromatic laser light pulses 26. Monochromatic laser light pulses 26 may also be referred to as narrow-band laser light pulses or laser light pulses of discrete wavelengths. The wavelength of monochromatic laser light pulses 26 may be invariable or variable and may, for example, be set to a wavelength between 500 and 1600 nm, preferably between 700 and 1000 nm. An example of a suitable laser unit is an ultra-short pulse laser, in particular a titanium-sapphire laser, which generates laser light pulses in the near infrared region.

Monochromatic laser light pulses 26 pass through a spectrally broadening element 28, which may, for example, be a microstructured optical element, in particular a microstructured light-conducting fiber as known from the prior art cited at the outset. Spectrally broadening element 28 causes monochromatic laser light pulses 26 to broaden spectrally in such a way that white-light laser pulses 30 exit spectrally broadening element 28. White-light laser pulses 30 have a broad continuous wavelength spectrum, which may, for example, extend through a plurality of colors distinguishable by the naked eye. White-light laser pulses 30 may be exclusively in the visible region, in the visible and near infrared region, or exclusively in the near infrared region. Due to dispersion effects caused, for example, by normal dispersion in spectrally broadening element 28, light components of different wavelengths of white-light laser pulses 30 are offset in time from one another, so that white-light laser pulses 30 temporally smeared or broadened in time, or have a wide distribution in time. In other words, photons of different spectral colors of one of white-light laser pulses 30 pass a given point at different times.

White-light laser pulses 30 pass through a spectrally dispersive element 32 which, for example, may take the form of an acousto-optical tunable filter (AOTF). Spectrally dispersive element 32, which may also be referred to as optical element 32, separates laser light of different wavelength intervals from the continuous spectrum of white-light laser pulses 30, so that spectrally dispersed laser light pulses 34 exit spectrally dispersive element 32. Spectrally dispersed laser light pulses 34 have continuous wavelength spectra and are spectrally spaced-apart from one another, so that light pulses of different wavelengths successively enter a compensation unit 36. Spectrally dispersive element 32 may be designed such that it only allows light of a predetermined wavelength interval to pass therethrough at any one time, or such that it allows light of a plurality of predetermined wavelength intervals to pass simultaneously therethrough.

Using dispersion effects opposite to those produced in spectrally broadening element 28, such as, for example, using anomalous dispersion, compensation unit 36 causes spectrally dispersed and temporally offset laser light pulses 34 to be once more offset in time, and in such a way that time-discrete white-light laser pulses 38 having a narrow temporal distribution exit compensation unit 36. In particular, discrete white-light laser pulses 38 do not have components which are offset in time from one another. In other words, compensation unit 36 causes photons of different spectral colors of one of white-light laser pulses 38 to pass a given point at the same time.

In this context, the statement that the light components are not offset in time from one another; i.e., that they are simultaneous, means that they are at least nearly not offset from one another. In this context, this means that the time offset between a first wavelength packet of one of white-light laser pulses 38 and another wavelength packet of the respective white-light laser pulse 38 is less than the lower time-resolution limit of a detector of microscope 40. If the wavelength packets exhibit a residual offset, this offset cannot be resolved by the detector, and the wavelength packets are classified as arriving simultaneously Time-discrete white-light laser pulses 38 are coupled into microscope 40, for example, via a light-conducting fiber. White-light laser pulses 38 are imaged by a first lens 42 onto an illumination pinhole 44. A beam splitter 46 directs white-light laser pulses 38 toward a second lens 48, which produces a parallel light beam having a beam axis 49. The light beam composed of white-light laser pulses 38 strikes a scanning device 50, which deflects white-light laser pulses 38 toward a third lens 51 using, for example, one or more mirrors. Scanning device 50 allows a sample 62 to be optically scanned by white-light laser pulses 38.

Disposed between third lens 52 and sample 62 are a fourth lens 54 and an objective 56 having a fifth lens 58 and a sixth lens 60, with the aid of which the illuminating light beam composed of white-light laser pulses 38 is formed for illuminating sample 62. Detection light coming from sample 62, which may include reflected illuminating light and/or fluorescent light, is returned through objective 56 to scanning device 50 and deflected by scanning device 50 toward a detection pinhole 64, the detection light passing through beam splitter 46 before detection pinhole 64 and striking a detector device 66 after detection pinhole 64, said detector device including at least one detector.

Figure 2:
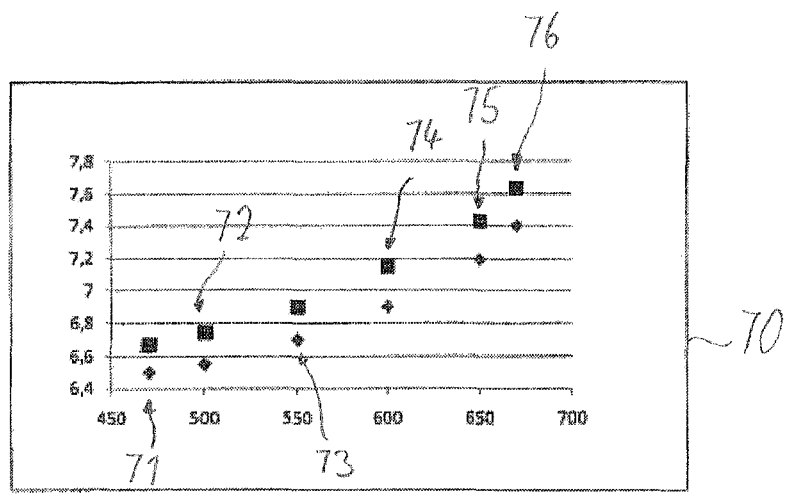
FIG. 2 is a wavelength-time diagram.

FIG. 2 shows a wavelength-time diagram, in which wavelengths from 450 nm to 700 nm are given on the X-axis. Plotted on the Y-axis are time values from 6.4 to 7.8 ns. In the diagram, there are shown a first light component 71, a second light component 72, a third light component 73, a fourth light component 75, a fifth light component 75, and a sixth light component 76. Light components 71, 72, 73, 74, 75, 76 have different colors, for example, red and blue. In the diagram, each of light components 71, 72, 73, 74, 75, 76 includes a rhombus and a square located vertically one above the other, the rhombus marking the beginning of a light pulse, and the square marking the end of a light pulse. The measurement of the time distribution of light components 71, 72, 73, 74, 75, 76 is performed after white-light laser pulses 30 containing temporally offset light components 71, 72, 73, 74, 75, 76 exit spectrally dispersive element 32. Light components 71, 72, 73, 74, 75, 76 are spectrally limited and spectrally spaced-apart from one another. The time offset between the individual light components 71, 72, 73, 74, 75, 76 is 50 to 1000 ps. Thus, the wavelength-time diagram shows the time offset between light components 71, 72, 73, 74, 75, 76 of different wavelengths of white-light laser pulses 30.

Figure 3:
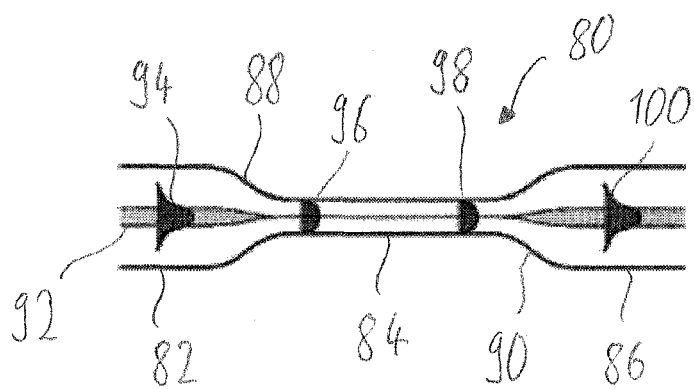
FIG. 3 is a view showing a compensation element.

FIG. 3 shows an exemplary embodiment of a compensation element 80 disposed in compensation unit 36. In addition to compensation element 80, compensation unit 36 may have further compensation elements 80 disposed therein in parallel or series to one another. Furthermore, compensation unit 36 may form part of a compensation device which includes further compensation units in addition to this compensation unit 36.

Compensation element 80 is formed by a microstructured light-conducting fiber whose microstructure is composed of tubes, cannulas or channels. Compensation element 80 has an input section 82 into which are coupled white-light laser pulses 30 containing temporally offset light components. Inside compensation element 80, white-light laser pulses 30 pass through a tapered section 84 and exit from compensation element 80 at an output section 86. Compensation element 80 may be fused, in particular spliced, at its input section 82 and/or at its output section 86 to one or more further light-conducting fibers, or may partially or completely replace the same.

In this exemplary embodiment, the transitions from input section 82 to tapered section 84 and from tapered section 84 to output section 86 are designed to be adiabatic. In particular, there are formed a first adiabatic transition 88 and a second adiabatic transition 90. In this context, "adiabatic" means that the transition is continuous and not stepped. Adiabatic transitions 88, 90 of compensation element 80 help the light being coupled in in an efficient and stable manner.

Compensation element 80 may be designed to maintain polarization, for example by breaking its rotational symmetry. Compensation element 80 may also be referred to as ultra-thin glass fiber or tapered fiber. The material of compensation element 80 may, for example, exhibit an anomalous dispersion of 500 ps/nm/km as averaged over the respective spectral region. There may be an intensity loss of, for example, 45 dB/km, which means a loss of 10% or more over a distance of 10 m. The zero dispersion may be shifted to the blue. The tapering of the compensation element may also be referred to as thickness modulation. Such thickness modulation may be more complex than in the exemplary embodiment shown. Thickness modulation can be used, in particular, to improve the injection efficiency. Compensation element 80 may be terminated at both ends. Specifically, it may be fused, in particular spliced, to a conventional glass fiber, or may completely replace the same. The termination may be accomplished by attaching connectors or by fusion, in particular by splicing.

The light enters compensation element 80 at input section 82 and propagates within the light-conducting fiber in a fiber core 92 thereof. The light injected as a light pulse 94 is passed through the first adiabatic transition 88, whereby the shape of light pulse 94 turns into the shape of light pulse 96. In tapered section 84, a dispersion-compensated light pulse 98 is then formed in the ultra-thin section of the fiber, particularly in tapered section 84. The light is further passed through second adiabatic transition 90 into a thick section of the fiber, in which a light pulse 100 is formed, whereupon the light exits at output section 86.

Figure 4:
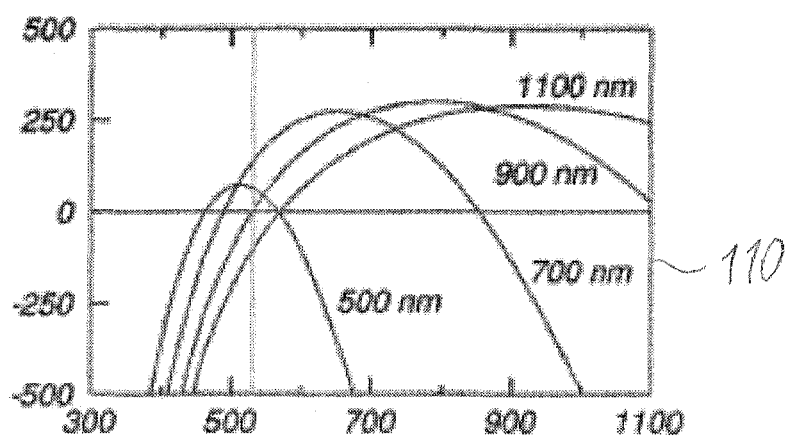
FIG. 4 is a wavelength-dispersion diagram.

FIG. 4 is a wavelength-dispersion diagram showing a plurality of curves labeled with values of thickness. The thickness values refer to the thicknesses of tapered sections 84 of different compensation elements 80. Thus, the wavelength-dispersion diagram shows the wavelength-dependent dispersion of different compensation elements 80. Specifically shown is the wavelength-dependent dispersion for diameters of 500 nm, 700 nm, 900 nm and 1100 nm of tapered section 84. The horizontal line marks the zero dispersion, and the vertical line indicates the 532 nm wavelength.

FIG. 4 illustrates that the dispersion can be adjusted through the selection of the diameter of tapered section 84. It is possible, in particular, to use a wide dispersion range, in particular, the entire dispersion range, of compensation element 80 for compensating the time offset between light components 71, 72, 73, 74, 75, 76 of white-light laser pulses 30. This allows a great degree of freedom for the design and compensation in the use of compensation element 80.

Figure 5:
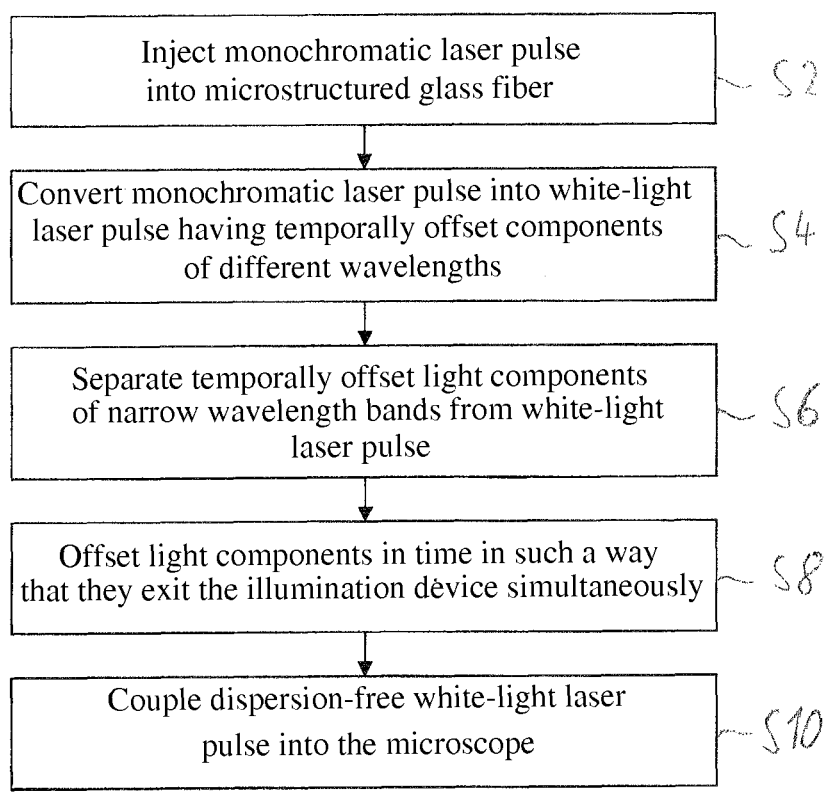
FIG. 5 is a flow chart of a method for producing an illuminating light beam for a microscope.

FIG. 5 shows a flow chart of a method for producing an illuminating light beam for microscope 40.

In a step S2, monochromatic laser light pulses 26 are injected as narrow-band laser light into spectrally broadening element 28, for example, into a microstructured glass fiber.

In a step S4, the microstructured glass fiber converts monochromatic laser light pulse 26 into a white-light laser pulse 30 having light components 71, 72, 73, 74, 75, 76 which are offset in time from one another. The time offset is caused, for example, by normal dispersion.

In a step S6, temporally offset light components 71, 72, 73, 74, 75, 76 of narrow wavelength bands are separated from white-light laser pulse 30.

In a step S8, light components 71, 72, 73, 74, 75, 76 are be offset in time, in particular, delayed, in such a way that they exit illumination device 20 simultaneously. The time delay is caused, for example, by anomalous dispersion. In this context, the statement that light components 71, 72, 73, 74, 75, 76 exit illumination device 20 simultaneously means, for example, that they exit the illumination device within an interval less than 50 to 200 ps, since this corresponds to the time-resolution limit of the detector of detector device 66. The resolution limit of the detector takes into account the total response time of the detector, including the processing electronics. The pulse widths of white-light laser pulses 38 should then be less than one-fourth or one-tenth of the overall system response including the response time of the electronics and that of the detector.

In a step S10, a dispersion-free white-light laser pulse 38, in particular one whose light components of different wavelengths are not or at least nearly not offset in time from one another, is coupled into microscope 40.

Providing white-light laser pulses 38 without time offset between its light components 71, 72, 73, 74, 75, 76 facilitates the development of two fluorescence curves, in particular in FLIM applications. Moreover, samples can be analyzed with a plurality of dyes or fluorescence curves in a simplified manner. A saving in time is achieved by the capability of analyzing samples with two or more dyes or fluorescence curves simultaneously. Further, it is possible to carry out resonance experiments in which two dyes act simultaneously, such as in a Fluorescence Resonance Energy Transfer (FRET) method.

Moreover, microscope 40 may be designed to be capable of multi-photon excitation. Alternatively, there may be provided a wide-field microscope that uses compensation unit 36 and, in particular, allows time-resolved measurement. Furthermore, the illuminating light beam of white-light laser pulses 38 without time offset may also be used in other microscopes or for other microscopic methods, such as FLIM.

LIST OF REFERENCE NUMERALS 20 illumination device
22 laser device
24 laser unit
26 monochromatic laser light pulses
28 spectrally broadening element
30 white-light laser pulses having temporally offset light components
32 optical element
34 spectrally dispersed laser light pulses
36 compensation unit
38 white-light laser pulses
40 microscope
42 first lens
44 illumination pinhole
46 beam splitter
48 second lens
49 beam axis
50 scanning device
52 third lens
54 fourth lens
56 objective
58 fifth lens
60 sixth lens
62 sample slide
64 detection pinhole
68 detector device
70 wavelength-time diagram;
71 first light component
72 second light component
73 third light component
74 fourth light component
75 fifth light component
76 sixth light component
80 compensation element
82 input section
84 tapered section
86 output section
88 first adiabatic transition
90 second adiabatic transition
92 fiber core
94 light pulse in the thick section of the fiber
96 light pulse in the ultra-thin section of the fiber
98 dispersion-compensated light pulse in the ultra-thin section of the fiber
100 dispersion-compensated light pulse in the thick section of the fiber
110 wavelength-dispersion diagram
S2-S10 steps two through ten

What is claimed is:

1. An illumination device for a microscope having a detector, the illumination device comprising:
    a laser unit that generates at least one broadband white light laser pulse having light components of different wavelengths being offset in time from each other;
    an acousto-optical tunable filter (AOTF) that separates different wavelength intervals from the at least one broadband white light laser pulse received from the laser unit to generate spectrally dispersed laser light pulses having continuous wavelength spectra and being spectrally spaced-apart from one another; and
    a compensation unit for further spectrally dispersing and temporally offsetting the spectrally dispersed laser light pulses received from the AOTF to generate time discrete white light laser pulses wherein a time offset between a first wavelength packet of one of the time discrete white light laser pulses and another wavelength packet of the respective time discrete white light laser pulses is less than a predetermined time resolution limit of the detector of the microscope.

2. The illumination device recited in claim 1, wherein the compensation unit includes a compensation element in the form of a microstructured light-conducting fiber.

3. The illumination device as recited in claim 1, wherein the compensation unit includes a compensation element in the form of an ultra-thin glass fiber or a tapered fiber.

4. The illumination device as recited in claim 2, wherein the microstructured light-conducting fiber has a glass core or an air core.

5. The illumination device as recited in claim 2, wherein dispersion of the microstructured light-conducting fiber is determined by a structure and/or length thereof.

6. The illumination device as recited in claim 5, wherein the structure of the microstructured light-conducting fiber changes adiabatically.

7. The illumination device as recited in claim 2, wherein the microstructured light-conducting fiber is a rotationally asymmetrical fiber.

8. A microscope for examining an object, wherein said microscope is coupled to the illumination device of claim 1.

9. The microscope as recited in claim 8, wherein said microscope is a confocal scanning microscope.

10. A method for producing an illuminating light beam for a microscope having a detector, the method comprising:

generating, in a laser unit, a broadband white light laser light pulse having light components of different wavelengths which are offset in time from one another;

generating in an acousto-optical tunable filter (AOTF), from the broadband white light laser light pulse received from the laser unit, spectrally dispersed laser light pulses having continuous wavelength spectra and being spectrally spaced-apart from one another; and generating, in a compensation unit, time discrete white light laser pulses by further spectrally dispersing and temporally offsetting the spectrally dispersed laser light pulses received from the AOTF, wherein a time offset between a first wavelength packet of one of the time discrete white light laser pulses and another wavelength packet of the respective time discrete white light laser pulses is less than a predetermined time resolution limit of the detector of the microscope.

\* \* \* \* \*